United States Patent [19]
Weng et al.

[11] Patent Number: 5,269,297
[45] Date of Patent: Dec. 14, 1993

[54] ULTRASONIC TRANSMISSION APPARATUS

[75] Inventors: Li Weng, Ramsey, N.J.; Robert M. Scribner, Broomfield, Colo.

[73] Assignee: Angiosonics Inc., Wayne, N.J.

[21] Appl. No.: 842,529

[22] Filed: Feb. 27, 1992

[51] Int. Cl.[5] .............................................. A61H 23/00
[52] U.S. Cl. .................................. 128/24 AA; 604/22
[58] Field of Search .................. 128/24 AA; 604/22; 606/128; 433/119; 310/15, 328

[56] References Cited

U.S. PATENT DOCUMENTS

| | | | |
|---|---|---|---|
| 2,748,298 | 5/1956 | Calosi et al. | 128/24 AA X |
| 3,526,219 | 9/1970 | Balamuth | 128/24 AA X |
| 4,531,934 | 7/1985 | Kossonsky et al. | 606/128 X |
| 4,646,725 | 3/1987 | Moasser | 128/24 AA |
| 4,748,971 | 6/1988 | Borodulin et al. | 128/24 AA |
| 4,750,488 | 6/1988 | Wuchinich et al. | 606/128 |
| 4,823,793 | 4/1989 | Angulo et al. | 128/24 AA |
| 5,058,570 | 10/1991 | Idemoto et al. | 128/24 AA |
| 5,112,300 | 5/1992 | Ureche | 128/24 AA |
| 5,123,903 | 6/1992 | Quaid et al. | 128/24 AA X |
| 5,163,421 | 11/1992 | Bernstein et al. | 606/159 X |

Primary Examiner—Lee S. Cohen
Assistant Examiner—Samuel Gilbert
Attorney, Agent, or Firm—Curtis, Morris & Safford

[57] ABSTRACT

A horn connectable to an energy source to amplify ultrasound displacement is connected to a transmitter formed of material having relatively high mechanical Q for transmitting ultrasonic energy therethrough at a frequency f, the transmitter having a horn-shaped configuration of length that is a multiple of a half-wavelength $\lambda/2$, and preferably this horn-shaped configuration is comprised of multiple horn segments, each of a length substantially equal to a multiple of $\lambda/2$, where $\lambda=c/f$ (c is the speed of sound in the high Q material). The transmitter has a proximal end of cross-sectional diameter $D_1$ connected to the horn and a distal end of cross-sectional diameter $D_2$, where $D_1>D_2$. Ultrasonic energy transmitted through the transmitter drives a tip which is coupled to the transmitter by means of a flexible connector.

51 Claims, 9 Drawing Sheets

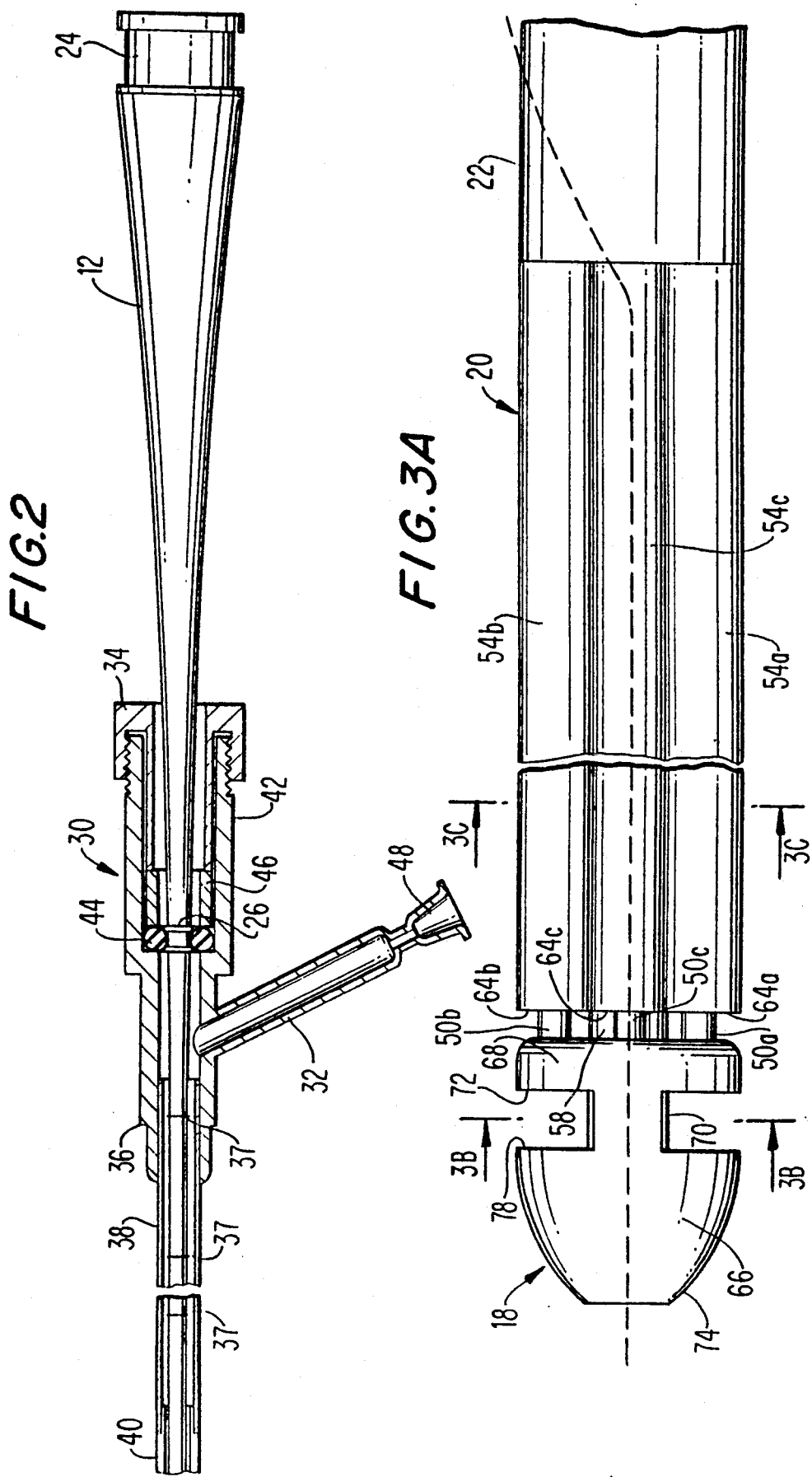

ULTRASONIC TRANSMISSION APPARATUS

BACKGROUND OF THE INVENTION

This invention relates to ultrasonic transmission apparatus and, more particularly, to such apparatus which transmits ultrasonic energy from a source to a distal tip with minimal loss, and which is particularly adaptable for medical applications.

The field of balloon angioplasty provides an established technique for reducing vascular obstructions caused by thrombi and plaque deposits. Here, a catheter having an inflatable balloon at its distal end is inserted into a patient's blood vessel and then, by use of a guide wire, in cooperation with an observation system, the catheter is advanced until it reaches the obstruction (e.g. a thrombus) in question. Then, the balloon is inflated with the hope of reducing the obstruction. Unfortunately, balloon angioplasty, although offering a desirable alternative to arterial bypass surgery, suffers significant drawbacks. For example, the procedure is neither effective nor safe in cases of thrombus. Thrombus often is not destroyed by the inflated balloon, thus resulting in relatively quick re-occlusion. In addition, balloon angioplasty often is accompanied by significant damage to the blood vessel which further stimulates thrombus formation and re-occlusion.

Other catheter-based procedures have been proposed as alternatives to bypass surgery, such as laser-type angioplasty, mechanical drills and, most recently, ultrasonic angioplasty. One example of ultrasonic angioplasty apparatus is described in copending application Ser. No. 449,465, assigned to the same assignee as the present invention.

In a typical ultrasonic angioplasty device, a long, thin ultrasonic transmitter connects a tip at its distal end to a power source at its proximal end. Using standard angioplasty techniques, this transmitter is inserted into and guided through the patient's blood vessel until the distal tip arrives at the occlusion. Then, energization of the power source produces ultrasonic displacement that is transmitted to the tip, resulting in destruction of the thrombus. However, and as found in the ultrasonic angioplasty apparatus described in U.S. Pat. No. 4,870,953, the transmission of ultrasonic energy through the ultrasonic transmitter could generate an inordinate amount of heat which, if not removed, could result in serious damage to the patient's blood vessels. Accordingly, the apparatus described in U.S. Pat. No. 4,870,953 provides a cooling arrangement in which the ultrasonic transmitter is disposed in a cooling bath, namely a catheter that is flushed with a physiologic solution to cool the entire transmitter.

It has been found that heat generation is common to most materials heretofore used for ultrasonic angioplasty because those materials produce significant attenuation of the ultrasonic energy. Consequently, acoustic energy is transformed to thermal energy. For the purpose of coronary procedures, the ultrasonic energy must be transmitted over a distance on the order of about 125-150 cm.; and the attenuation presented by this length of material requires an extremely high input energy level in order for sufficient ultrasonic displacement to be produced at the tip. Therefore, the heat generated by the typical ultrasonic angioplasty device increases the probability of material fatigue which may result in fracture of the device while in use.

The aforementioned patent application 449,465 is directed to a novel arrangement which overcomes these drawbacks, disadvantages and hazards. As disclosed therein, the ultrasonic transmitter is formed of material having a high mechanical Q, thus minimizing the attenuation experienced by the ultrasonic energy as it is transmitted through this transmitter and thereby minimizing heat generation. Preferably, aluminum or an aluminum alloy having a mechanical Q greater than 50,000 is used. Examples of suitable alloys include duralumin, hiduminium, AL-7075, AL-2024 and AL-6061. The generation of heat is substantially obviated; and it no longer is necessary to use an ultrasonic source of high energy levels in order to drive the transmitter.

While the aforementioned ultrasonic angioplasty device obtains benefits and results not previously realized, further investigation into ultrasonic angioplasty has led to certain observations, culminating in the invention disclosed herein.

It has been found that the cross-sectional area of the ultrasonic transmitter directly affects the attenuation of the ultrasonic energy transmitted thereby. That is, a greater cross sectional diameter results in less attenuation of the transmitted ultrasonic energy, thereby permitting the use of an ultrasonic energy source having a lower energy level. But, an ultrasonic transmitter of greater cross-sectional diameter results in a more rigid transmission member which may not be able to follow easily the bends inherent in typical blood vessels.

It also has been found that an ultrasonic transmitter of reduced cross sectional diameter formed of high mechanical Q material may be susceptible to easy fracture or fatigue. Thus, although a very thin ultrasonic transmitter may exhibit 14 sufficient flexibility, it also presents an extremely high risk of breakage due to fatigue and to significant bending thereof as it follows a blood vessel.

It has been observed, that, when a physician uses a typical ultrasonic angioplasty device, he manually guides it into the patient's blood vessel and, more often than not, grasps a portion of the transmission member while ultrasonic energy is transmitted therethrough. This presents a problem because it results in substantial damping of ultrasonic displacement, thereby seriously reducing the operating efficiency of the device.

Although many conventional ultrasonic medical instruments, such as an ultrasonic scalpel, operate at frequencies in the range 20-30 kHz, it has been found that such frequencies do not permit maximum displacement at the tip of the apparatus when the device is bent. However, the higher frequencies needed for more optimum displacement present more difficult design parameters, they result in greater attenuation of the transmitted ultrasonic energy and, for the same displacement, they produce greater internal stress which increases the tendency of the transmitter to fracture due to fatigue. On the other hand, however, a higher ultrasonic frequency permits the transmitter to be subjected to a sharper bend without as significant an energy loss as at lower frequencies and, thus, the use of such higher frequencies in an ultrasonic angioplasty device permits that device to be used in blood vessels and lumens having tighter turns.

It also has been observed, that since patient safety is of the highest priority, care must be taken in the design of the ultrasonic angioplasty device to minimize hazards and risk of injury to the patient in the event of a malfunction or break in the device.

OBJECTS OF THE INVENTION

Therefore, it is an object of the present invention to provide improved ultrasonic transmission apparatus which minimizes the attenuation of ultrasonic energy transmitted therethrough, thus permitting the use of an ultrasonic source of reduced energy level.

Another object of this invention is to provide ultrasonic transmission apparatus which finds particular application in coronary procedures as well as in other procedures in which the apparatus follows curved or tortuous paths.

A further object of this invention is to provide an ultrasonic transmitter for generating optimal ultrasonic displacement at its distal tip while being connected at its proximal end to an ultrasonic source of reduced energy level.

Still another object of this invention is to provide an ultrasonic angioplasty device having desirable flexibility, maximum tip displacement and minimal energy loss as ultrasonic energy is transmitted from a suitable source to the tip.

An additional object of this invention is to provide an ultrasonic angioplasty device formed of material having a high mechanical Q and exhibiting good resistance to fatigue and fracture.

It is a further object of this invention to provide an ultrasonic angioplasty device which generates minimal heat and is provided with a safety feature to prevent injury to the patient in the event that the angioplasty device breaks.

Another object of this invention is to provide an ultrasonic angioplasty device having a distal tip configured to maximize cavitation in the fluid in which the device is used.

Various other objects, advantages and features of the present invention will become readily apparent from the ensuing detailed description, and the novel features will be particularly pointed out in the appended claims.

SUMMARY OF THE INVENTION

In accordance with this invention, improved ultrasonic transmission apparatus is provided with a horn connectable to an energy source for amplifying ultrasound displacement and a transmitter formed of material having relatively high mechanical Q for transmitting ultrasonic energy therethrough at a frequency f. The transmitter exhibits a horn-shaped configuration of $l_2$ length that is substantially a multiple of a half-wavelength of $\lambda/2$, and preferably the transmitter is comprised of multiple horn segments, each having a length substantially equal to a multiple of $\lambda/2$, where $\lambda$ equals c/f and c is the speed of sound in the material. The transmitter has a proximal end of cross-sectional diameter $D_1$ connected to the horn and a distal end of cross-sectional diameter $D_2$ wherein $D_1 > D_2$. A tip driven by the ultrasonic energy is coupled to the transmitter by way of a flexible connector which transmits ultrasonic energy therethrough. In a preferred embodiment, the flexible connector is comprised of plural wires, each of a diameter less than $D_2$, and each wire having a first end connected to the distal end of the transmitter and a second end connected to the tip for transferring to the tip ultrasonic energy received from the transmitter.

The wires of the flexible connector may be coupled directly to the distal end of the transmitter; but in one embodiment, a base member is provided for effecting this connection. In this embodiment, the base member comprises a generally cylindrical housing having at one end a central recess of a diameter substantially equal to $D_2$ to receive the distal end of the transmitter, and at the other end plural recesses each of a diameter substantially equal to that of each wire for receiving the first ends of the plural wires.

As an aspect of this invention, the plural wires are isolated from each other, as by being disposed in respective tubular channels which may be formed of individual tubes or, alternatively, the tubular channels may be comprised of a multi-lumen conduit. Preferably, the tubular channels are open at their opposite ends and are formed of flexible material such that hey and the wires disposed therewithin are adapted to follow the bends of a patient's blood vessel. The open ended tubular channels permit the introduction thereinto of a suitable fluid, such as a saline solution. This solution reduces the ultrasonic load on the transmitter; and additionally prevents backflow of, for example, the patient's blood.

As a feature of this invention, a sleeve is disposed about at least those segments of the transmitter expected to be inserted into the blood vessel. It is expected that in use, the transmitter will be inserted into a guide catheter that is inserted into the patient's blood vessel. The distal end of the sleeve is secured to the tubular channels surrounding the wires, thereby providing a conduit for the aforementioned fluid.

As an aspect of this feature, fluid is supplied to the sleeve by an input conduit coupled thereto, and a valve in fluid communication with the proximal end portion of the sleeve acts to prevent backflow of fluid through the sleeve. In a preferred embodiment, the input conduit includes a coupling channel for coupling the proximal end portion of the sleeve to the horn, and the valve comprises a manually tightened cap coaxial with the horn and disposed over the coupling channel and the horn and located at a node of longitudinal ultrasonic vibration.

As another aspect of this invention, a protective cover or sheath is disposed over at least one segment at the proximal end of the transmitter, and terminates substantially at a node of ultrasonic vibration in the transmitter. Hence, a user, such as a physician, is enabled to grasp the proximal end when guiding the transmitter into a lumen without contacting the transmitter directly. This avoids substantial damping of ultrasonic vibrations of the transmitter. Preferably, the segment (or segments) over which the sheath is disposed, is provided with annular shoulders located at ultrasonic vibration nodes to contact the sheath in the event the sheath is deformed. When the apparatus is disposed in a guide catheter which is inserted into the patient's blood vessel, the doctor advances the transmitter so that the distal end of the apparatus, namely the tip, extends beyond the guide catheter into contact with, or proximate, a thrombus or other obstruction to be removed. The length of the protective sheath preferably is a function of the location of the nodes of ultrasonic vibration. Since, in a preferred embodiment, this sheath is relatively rigid, its length influences the overall flexibility of the transmitter and it should be as short as is practical because its rigidity tends to reduce the flexibility of the transmitter. However, its length should be equal to the distance the physician is expected to move the tip beyond the end of the guide catheter.

Preferably, fluid is supplied from a suitable source to the protective sheath which is in fluid communication with the sleeve and which, in turn, is in fluid communication with the tubular channels surrounding the wires of the flexible connector.

In a preferred embodiment, the transmitter is formed of aluminum and the wires of the flexible connector are formed of titanium.

As another feature of this invention, the tip exhibits increased surface area so as to increase cavitation. In one embodiment, the tip is comprised of proximal and distal cylindrical portions which are interconnected by an intermediate portion having a thickness less than the diameter of each of the proximal and distal portions, thus increasing the surface area of the tip. Different tip shapes and configurations are disclosed. For example, the distal portion of the tip may be of substantially truncated semi-spheroid shape, and the proximal portion may be of cylindrical shape. The distal portion may include a concave face. In another example, the distal portion of the tip may be mushroom-shaped. In yet another example, the distal portion of the tip may exhibit a "double mushroom" shape.

BRIEF DESCRIPTION OF THE DRAWINGS

The following detailed description, given by way of example and not intended to limit the present invention solely thereto, will best be understood in conjunction with the accompanying drawings in which:

FIG. 2 is a sectional view of the sleeve, protective sheath and fluid coupling channel in the vicinity of the proximal end of the ultrasonic transmission apparatus shown in FIG. 1;

FIGS. 3A–3D are views of respective portions of the flexible connector and tip of the ultrasonic transmission apparatus;

DETAILED DESCRIPTION OF PREFERRED EMBODIMENTS

Figure 1:
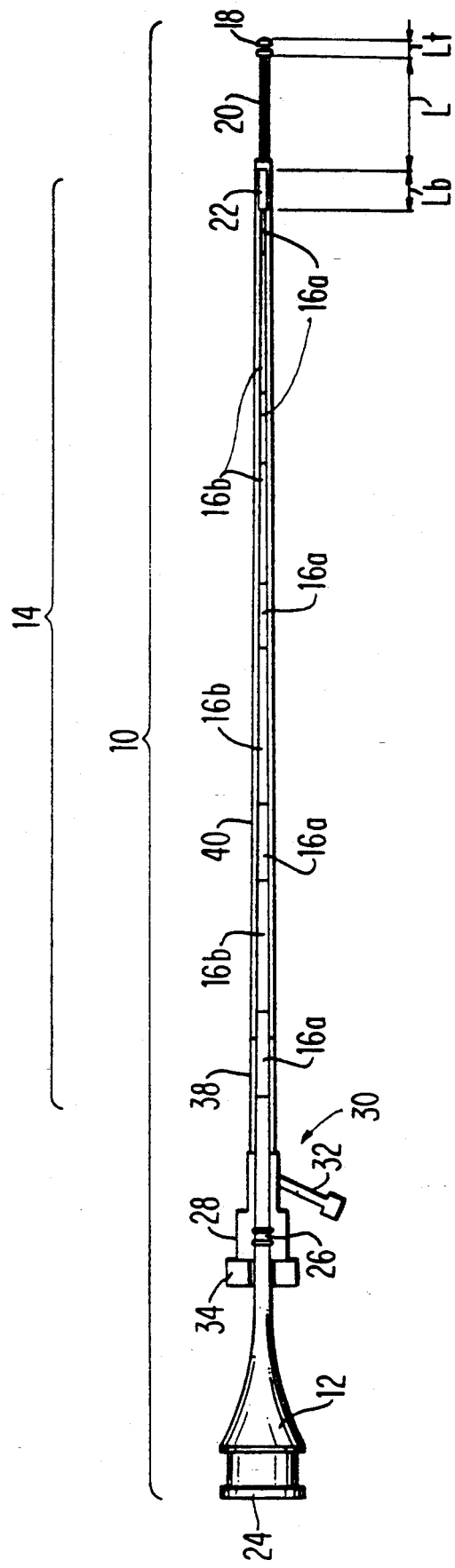
FIG. 1 is a side view of ultrasonic transmission apparatus in accordance with the present invention.

Referring now to the drawings, wherein the like reference numerals are used throughout, and in particular to FIG. 1, there is illustrated a preferred embodiment of ultrasonic transmission apparatus in accordance with the present invention. For convenience, this apparatus is shown and described herein in the environment of an ultrasonic angioplasty device readily adapted to be guided into a lumen of a patient, referred to generally herein as the patient's blood vessel, for the purpose of destroying a thrombus therein. It will be appreciated, however, that the ultrasonic transmission apparatus disclosed herein admits of different applications and need not be limited solely to coronary thrombosis angioplasty or even to medical applications.

As shown in FIG. 1, ultrasonic transmission apparatus 10 is comprised of a horn 12, a transmitter 14, a tip 18 and a flexible connector 20 for connecting tip 18 to transmitter 14. FIG. 1 also illustrates surrounding tubing in which the ultrasonic transmission apparatus is disposed. The purpose and construction of this tubing is described hereinbelow.

A desirable objective of ultrasonic transmission apparatus 10 is to generate reciprocating movement of tip 18 along the longitudinal axis of the ultrasonic transmission apparatus, referred to as longitudinal displacement of the tip. The apparatus has been designed to provide maximum displacement of tip 18 while requiring minimal input energy to achieve that displacement. For example, desirable tip displacement is on the order of about $20\mu$ to $60\mu$ peak-to-peak, at ultrasonic frequencies, and in one application, this displacement is about $30\mu$. The overall length of the apparatus from the proximal end of horn 12 to tip 18 disposed at the distal end of the ultrasonic transmission apparatus generally is in the range of 100 to 150 cm., and for most patients, this length is about 140 cm for intracoronary procedures. In other applications, this length may be shorter or greater.

Figure 1A:
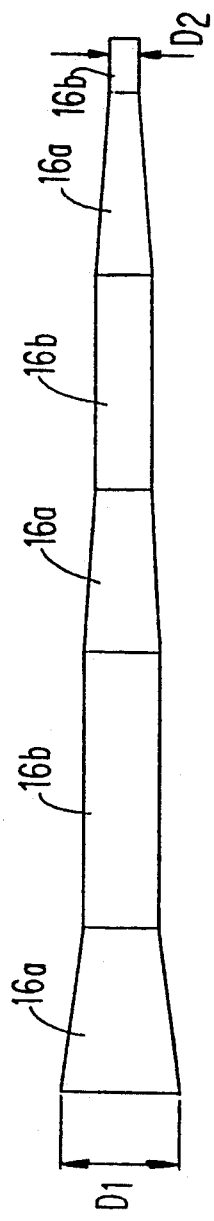
FIG. 1A illustrates the transmitter of the present invention.

It is appreciated that ultrasonic energy which is supplied to horn 12 from a suitable energy source will undergo substantial attenuation over the length of the ultrasonic transmission apparatus. Therefore, to achieve the desirable tip displacement without requiring very high (and potentially harmful) input energy transmitter 14 has been designed to minimize such attenuation. This is achieved by constructing transmitter 14 of a material having a very high mechanical Q, such as on the order of 50,000 or greater. One example of a suitable material is aluminum or an aluminum alloy, such as AL-7075, AL-2024, AL-6061, duralumin and hiduminium, as disclosed in copending application Ser. No. 449,465. In addition, in the preferred embodiment, transmitter 14 is formed of multiple horn segments distributed along the length thereof. The horn segments may be exponential, stepped, or exhibit other profiles or shapes known to those of ordinary skill in the art. Preferably, each segment has a length substantially equal to a multiple of $\lambda/2$, where $\lambda = c/f$, f is the frequency of the ultrasonic energy supplied to the transmitter and c is the speed of sound in the material. The horn segments need not exhibit equal lengths, and a thicker segment provides less attenuation than a thinner segment. Also, in the preferred embodiment, segments that are substantially straight, that is, where the diameter at the proximal end thereof is equal to the diameter at the distal end, are interspersed with the horn segments. Here too, the length of each straight segment is equal to a multiple of $\lambda/2$; and it is seen in FIG. 1A that horn segments 16a alternate with straight segments 16b. Such alternation of horn and straight segments results in what is referred to herein as a regular distribution of horn segments along the length of transmitter 14. The length of a horn segment 16a need not be equal to the length of an adjacent straight segment 16b; and it will be appreciated that segments 16b need not necessarily be straight.

The lengths of the horn and straight segments 16a and 16b at the proximal end of the transmitter may be longer than at the distal end because the larger diameter of these segments at the proximal end provides less displacement loss. Also, since the longer, thicker segments are less flexible, it is preferable in coronary applications for the distal end of the transmitter to be more flexible and thus follow the turns of the patient's blood vessel.

Figure 1B:
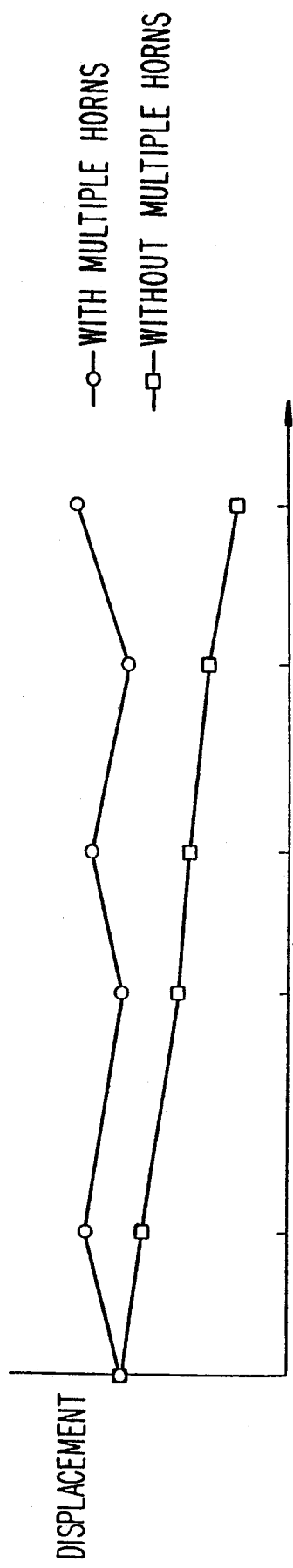
FIG. 1B is a graphical representation of the relationship between displacement and length of the transmitter of FIG. 1A.

It has been found that each horn segment 16a acts as a transformer analogous to an electrical transformer and functions to increase the displacement produced in response to a given level of input ultrasonic energy. A graphical representation of the manner in which the displacement along the length of transmitter 14 varies in response to a given input ultrasonic energy level is shown in FIG. 1B. Whereas each horn segment 16a tends to increase the displacement that may be produced in response to this input energy level, each interspersed, or straight segment 16b simply attenuates that displacement. The displacement at the distal end of the transmitter may be reduced relative to the displacement that may be produced at its proximal end, but it will be seen that this reduction, or attenuation, is far less than would otherwise be achieved if transmitter 14 was of constant, uniform cross-sectional dimension, as represented by the attenuation characteristic in FIG. 1B.

Since ultrasonic transmission apparatus 10 is intended to be used in a patient's blood vessel, its design is subject to inherent constraints. For example, the thickness or cross-sectional diameter, of transmitter 14 must be sufficient to be placed within the patient's blood vessel, and in particular, the transmitter must be thin enough to be disposed within a guide catheter.

As another example, transmitter 14 cannot be so thick as to be too rigid and thus not capable of following the normal turns and bends of a blood vessel. Although a very thin transmitter would satisfy the need for a flexible device that passes easily within the patient's blood vessel, a thin transmitter of constant cross-sectional diameter results in unacceptable attenuation of the ultrasonic displacement, thus requiring a much higher level of input ultrasonic energy to produce a desired displacement. In addition, even when material with a high mechanical Q is used, the amount of input energy which is needed for a thin transmitter of constant cross-sectional diameter to achieve the desired tip displacement generates heat which is harmful and presents a serious risk of injury to the patient. Furthermore, a material such as aluminum, although exhibiting a desirably high mechanical Q is relatively brittle; and the tensile stress exerted by its ultrasonic displacement in combination with the need for a thin transmitter to follow the turns and bends of a blood vessel may result in fracture of the transmitter.

The foregoing difficulties are minimized by providing alternate segments 16a and 16b, as illustrated, thus minimizing attenuation of the ultrasonic displacement, and permitting the cross-sectional diameter of transmitter 14 to be reduced from a relatively large diameter $D_1$ at its proximal end to a relatively small diameter $D_2$ at its distal end. Thus, that portion of transmitter 14 which must be flexible in order to follow the turns and bends of a patient's blood vessel, namely the distal portion, exhibits reduced diameter to enhance flexibility; and the use of horn segments (even at the distal end thereof) provides improved attenuation characteristics, as shown in FIG. 1B. In one embodiment, diameter $D_1$ at the proximal end of the first horn segment 16a is on the order of about 1.6 mm and diameter $D_2$ at the distal end of transmitter 14 is on the order of about 0.63 mm. Although a transmitter formed of a single horn-shaped configuration whose overall length is a multiple of $\lambda/2$ may be used, such as a single, continuously tapered member of 100-150 cm in length, this single horn segment does not provide attenuation characteristics as favorable as the preferred embodiment formed of horn and straight segments distributed substantially regularly along the length of the transmitter.

Although each horn and straight segment has a length equal to a multiple of $\lambda/2$, this multiple (m) need not be the same for each segment. Thus, the length of a segment may be recognized, generally, as $m_i\lambda/2$ where $i=1, 2, 3$, etc. However, since the length of each segment is a multiple of $\lambda/2$, it is seen that adjacent segments join at displacement antinodes. It will be appreciated that these junctions are relatively smooth and do not present discontinuities from one segment to the next. In one embodiment, transmitter 14 is of integral one-piece construction; and may be machined from a single block of material or, alternatively, may be extruded.

Returning to FIG. 1, horn 12 is coupled to the proximal end of transmitter 14 and, in the preferred embodiment, the horn and transmitter are of integral one-piece construction. Alternatively, however, the transmitter may be otherwise secured to the horn, as by a suitable adhesive, welding, screw or other mechanical means normally used to connect components in an ultrasonic device. Horn 12 is provided with a hand piece connector 24 at its proximal end for receiving and coupling thereto a hand piece, such as hand piece 86 shown in FIG. 4. This hand piece includes a conventional transducer to convert electrical energy to ultrasonic acoustic energy and thereby drive horn 12.

As also shown in FIG. 1, horn 12 is provided with a pair of annular shoulders 26 disposed at an ultrasonic displacement node (that is, the displacement node is located between shoulders 26), these shoulders being adapted to receive an O-ring, such as O-ring 44 shown in FIG. 2, for providing a fluid-tight seal in a fluid supply channel 28, as will be described. By providing shoulders 26 at a node, the presence of this seal does not significantly affect the displacement of transmitter 14.

The distal end of the transmitter is coupled to tip 18 by flexible connector 20. From the preceding discussion, it is appreciated that the distal end of ultrasonic transmission apparatus 10 is expected to be subject to greater bending angles than the remainder of the apparatus as it is inserted into and through a blood vessel. Consequently, flexible connector 20 should exhibit high flexibility, yet it should be strong enough to withstand internal stress created by the transmission of ultrasonic energy therethrough. These requirements are met by constructing flexible connector 20 as a plurality of thin wires secured to the distal end of transmitter 14. In the preferred embodiment, the flexible connector is formed of a plurality of titanium wires; and any suitable number of wires will suffice. Preferably, 3 or 4 parallel wires are used, and as described hereinbelow in conjunction with FIG. 3, an embodiment utilizing four wires is shown. The diameter of each wire is less than the cross-sectional diameter $D_2$ of the distal segment included in transmitter 14. In one practical embodiment the diameters of the titanium wires are uniform, and the diameter $D_3$ of each titanium wire is on the order of about 0.27 mm.

Optimally, each of these titanium wires is secured directly to the end face of the distal segment included in transmitter 14, or, alternatively, is integrally formed with the distal segment of the transmitter. Moreover, it would be best if each wire is configured as a horn to act as a transformer for the ultrasonic displacement transferred thereto. However, such direct connection of a titanium wire to or integral fabrication of such a wire with the distal end of transmitter 14 presents substantial mechanical and assembly difficulties; as does the forming of a thin titanium wire with a horn configuration. Accordingly, in the embodiment illustrated herein, a base member 22 is used to connect the titanium wires to the transmitter. The base member may be formed of the same material as transmitter 14 and as will be described in greater detail in FIG. 5, includes a central recess 92 (see FIG. 5A) to receive the distal segment of transmitter 14, and also includes a plurality of recesses 94a, 94b ,... to receive respective ones of the connector wires.

In addition, to facilitate assembly of the ultrasonic transmission apparatus, central recess 92 of base member 22 exhibits uniform diameter $D_2$ to receive distal segment 16b, which is a straight segment. The length of this distal segment and, thus, the length of recess 92, is less than $\lambda/2$. Accordingly, it will be appreciated from FIG. 1 that the last segment 16a upstream of base member 22 is a horn segment to act as an ultrasonic displacement transformer. Distal segment 16b (as best seen in FIG. 1A) which is inserted into recess 92 of base member 22, is of minimal length sufficient to provide a mechanically secure connection of the base member to transmitter 14. Since this distal segment 16b and the titanium wires attenuate the ultrasonic displacement, it is desirable to minimize the total length of this distal segment and the titanium wires. Nevertheless, if the length of flexible connector 20 is represented as L, the length of base member 22 is represented as $L_b$ and the length of tip 18 is represented as $L_t$ (as shown in FIG. 1), then $L+L_b+L_t=k \lambda'/2$, where k is an integer and $\lambda'$ is the effective wavelength in the section formed of the base member (described herein as aluminum), the flexible connector (described as titanium) and the tip (described as aluminum). In the example described herein, this effective wavelength is determined primarily by the wavelength in aluminum and the wavelength in titanium.

In use, it is expected that the wires comprising flexible connector 20 will bend to follow the configuration of the blood vessel in which the apparatus is used. Consequently, contact between adjacent wires is likely. Such contact produces unwanted damping of ultrasonic displacement and the generation of excessive heat. Accordingly, to prevent such contact, the titanium wires are isolated from each other, and in one embodiment, this is achieved by disposing the wires in respective tubular channels which may be formed of, for example, individual flexible tubes or, alternatively, a multi-channel (or multi-lumen) conduit. Such tubes or tubular channels may be formed of plastic, rubber or other conventional flexible material normally used in medical applications. As will be described below, such tubes or tubular channels provide not only mechanical isolation of the wires but also enable fluid to flow therethrough for the purpose of reducing the ultrasonic load on the transmitter, as well as preventing backflow of blood through the conduit in which the transmitter is disposed. This fluid, such as saline, reduces transverse vibration of the connector wires and provides lubrication for longitudinal displacement of the wires. Further description of flexible connector 20 is described in conjunction with FIGS. 3A-3D.

It is desirable to provide a plurality of wires in connector 20, even though, theoretically, only one wire will suffice, because a single wire may not be capable of transmitting sufficient ultrasonic energy at desirably thin diameters and because of the improved safety factor exhibited by plural wires. Since the material from which the wires are formed preferably exhibits a tensile strength coefficient higher than that of the material from which transmitter 14 is formed, the risk of fatigue due to ultrasonic movement and bending of the connector is relatively low. Nevertheless, by using plural wires, the likelihood that all of the wires will fracture simultaneously is minimal. Thus, since flexible connector 20 couples tip 18 to transmitter 14, the use of plural wires substantially minimizes the risk that the tip will break away from the transmitter.

In addition, it has been found that plural wires are capable of transmitting more ultrasonic energy therethrough. Hence, the input energy supplied to the apparatus may be reduced without decreasing the operating efficiency of the transmission apparatus.

Tip 18 is reciprocally driven at ultrasonic frequencies for the desirable objective of creating cavitation in the patient's blood vessel. When adjacent a thrombus, such cavitation tends to dislodge dead red blood cells which are trapped in the fiber matrix of the thrombus, thus dispersing the thrombus and eliminating the blockage. Furthermore, by reason of this cavitation, and particularly because of the shape of tip 18, the released red blood cells are returned harmlessly to the patient's blood stream and the fibers are destroyed. In other applications, however, cavitation may not be of significant importance and the tip will be suitably shaped.

Figure 6A:
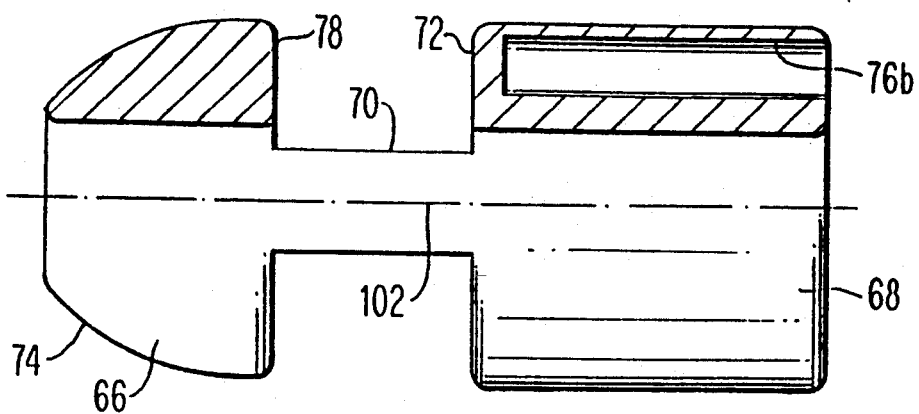
FIGS. 6A and 6B illustrate one embodiment of the tip that may be used with the present invention and FIG. 6C illustrates an alternative thereto.
Figure 6B:
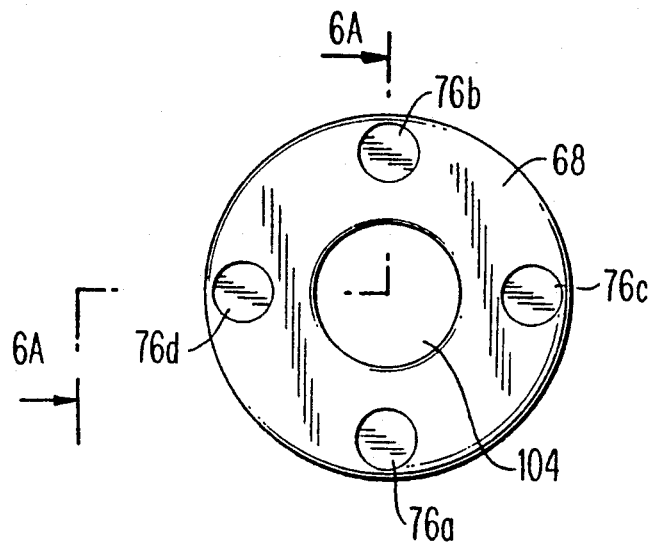
Figure 6C:
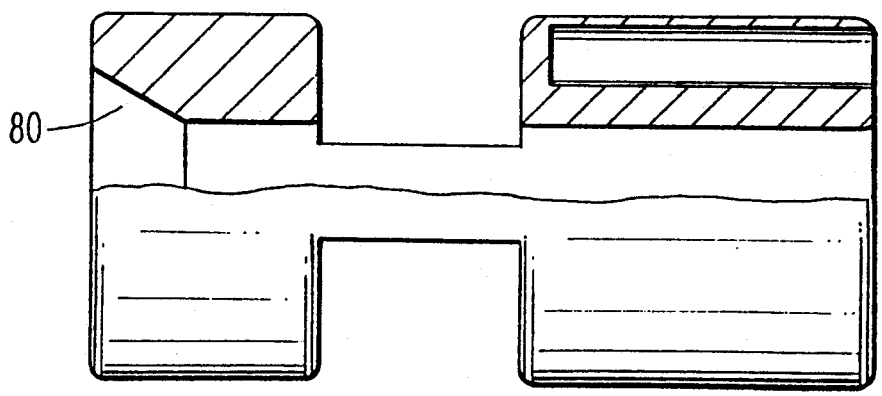

To optimize desirable cavitation, tip 18 is configured to have increased surface area. A preferred embodiment of the tip is illustrated in FIGS. 6A, 6B and 6C, and other embodiments are shown in FIGS. 7A-7K. As will be described, the preferred embodiment of tip 18 includes a proximal portion connected to the wires included in flexible connector 20, a distal portion having, preferably, a concave face, and an intermediate portion which connects the proximal and distal portions and which exhibits a thickness less than the diameter of either the proximal portion or the distal portion. In this embodiment, in addition to having a concave face, the distal portion of tip 18 is of a substantially truncated semi-spheroid shape, whereas the proximal portion is generally cylindrical. By providing the intermediate connecting portion between the proximal and distal portions with reduced thickness, a discontinuity in the surface of the tip is created, and this discontinuity increases the surface area in a direction perpendicular to the direction of displacement, as best shown in FIG. 6A.

As seen in FIG. 1, transmitter 14 is disposed in sleeve 40 which provides a channel for fluid to flow about the transmitter. Sleeve 40 is formed of flexible material, such as rubber, plastic or other suitable material commonly used in catheters for medical applications. The distal end of sleeve 40 is coupled to the tubular channels that surround the wires of flexible connector 20. This coupling may be achieved by an adhesive, by thermal bonding, or by other conventional means for providing a fluid tight connection of the sleeve to the tubular channels. Sleeve 40 also provides containment for transmitter 14 in the unlikely event that the transmitter fractures. Hence, the sleeve reduces risk of injury to the patient and facilitates rapid or emergency removal of the ultrasonic transmission apparatus from the patient's blood vessel.

The proximal end of sleeve 40 is coupled to protective sheath 38 with a fluid tight bond. The protective sheath provides a continuation of the fluid channel which surrounds transmitter 14. In a preferred embodiment, protective sheath 38 should be formed of material which is sufficiently strong as not to deform when grasped by a physician. It will be appreciated that when the illustrated ultrasonic transmission apparatus is advanced in a patient's blood vessel, there is a tendency for the physician or technician to grasp the proximal end of transmitter 14 for guiding the transmitter surely and stably. It is likely that the physician would contact a portion of the transmitter at a location other than a vibration node; and such contact would substantially damp the ultrasonic vibrations of the transmitter. However, by providing protective sheath 38, the grasping thereof by the physician will avoid contact between the physician's fingers and a segment 16a, 16b, and such avoidance of direct contact will prevent damping of the ultrasonic vibrations. Hence, protective sheath 38 performs a dual function, namely, it is included in the fluid conduit which surrounds transmitter 14, and it also provides protection against the damping of ultrasonic vibrations due to contact of the transmitter by the physician. It will be seen that the length of protective sheath 38 should be such that it ends at an ultrasonic vibration node. Also, its length preferably should be short because its rigidity reduces the flexibility of the transmitter, but nevertheless should be sufficient to permit the physician to advance the transmitter by an amount which moves tip 18 out of a guiding catheter with which the transmitter may be used and into proximity with a thrombus. Spacers 37 may be provided on transmitter 14 at displacement nodes to prevent sheath 38 from contacting the transmitter even if the sheath is deformed by the physician. These spacers may be shoulders formed on the transmitter, as shown in FIG. 2

It will be appreciated that, in normal use, the transmitter is inserted into and moved through a guide catheter of standard length. The guide catheter is provided with one or more hemostasis valves, located at positions such that these valves contact protective sheath 38 just as tip 18 emerges from the distal end of the guide catheter. At this location, the tip is spaced from the thrombus or obstruction. It is expected that the physician will advance the transmission apparatus to bring tip 18 adjacent to or in contact with the obstruction, and then he will energize the ultrasonic transmission apparatus. Thus, the transmitter is moved further into the guide catheter and the length of sheath 38 should be at least equal to this distance over which the transmitter is moved.

Since the cross-sectional diameter of transmitter 14 gradually decreases from its proximal end to its distal end, the interior volume of the fluid channel which surrounds the transmitter increases. Although it is desirable to reduce the diameter of the protective sheath and the sleeve gradually as well, this may result in an expensive custom design which would increase the cost of the apparatus. Consequently, protective sheath 38 exhibits uniform inner and outer diameters and, likewise, sleeve 40 exhibits uniform inner and outer diameters. Of course, the inner diameters of the sleeve and the protective sheath are greater than the maximum cross-sectional diameters of those segments 16a and 16b included therein so as to provide the fluid conduit surrounding these segments.

The proximal end of protective sheath 38 is in fluid communication with a suitable fluid source supplied thereto by a Y-shaped coupling channel 30. As illustrated in FIG. 1, and as will be described in connection with FIG. 2, coupling channel 30 is disposed about at least the distal portion of horn 12 and is coupled to protective sheath 38 by an input conduit 36. A syringe connector 32 functions to connect a syringe or other suitable source of fluid to coupling channel 30. Thus, fluid may flow from the fluid source to syringe connector 32, to coupling channel 30 and through input conduit 36 to protective sheath 38. Horn 12 exhibits an exponentially tapered profile and coupling channel 30 is secured in a fluid-tight manner to the horn. Such fluid-tight connection is provided by a cap 34 which cooperates with coupling channel 30 and O-ring 44 to achieve a fluid-tight seal. It will be appreciated that coupling channel 30 may be a conventional hemostatic adapter.

Figure 4:
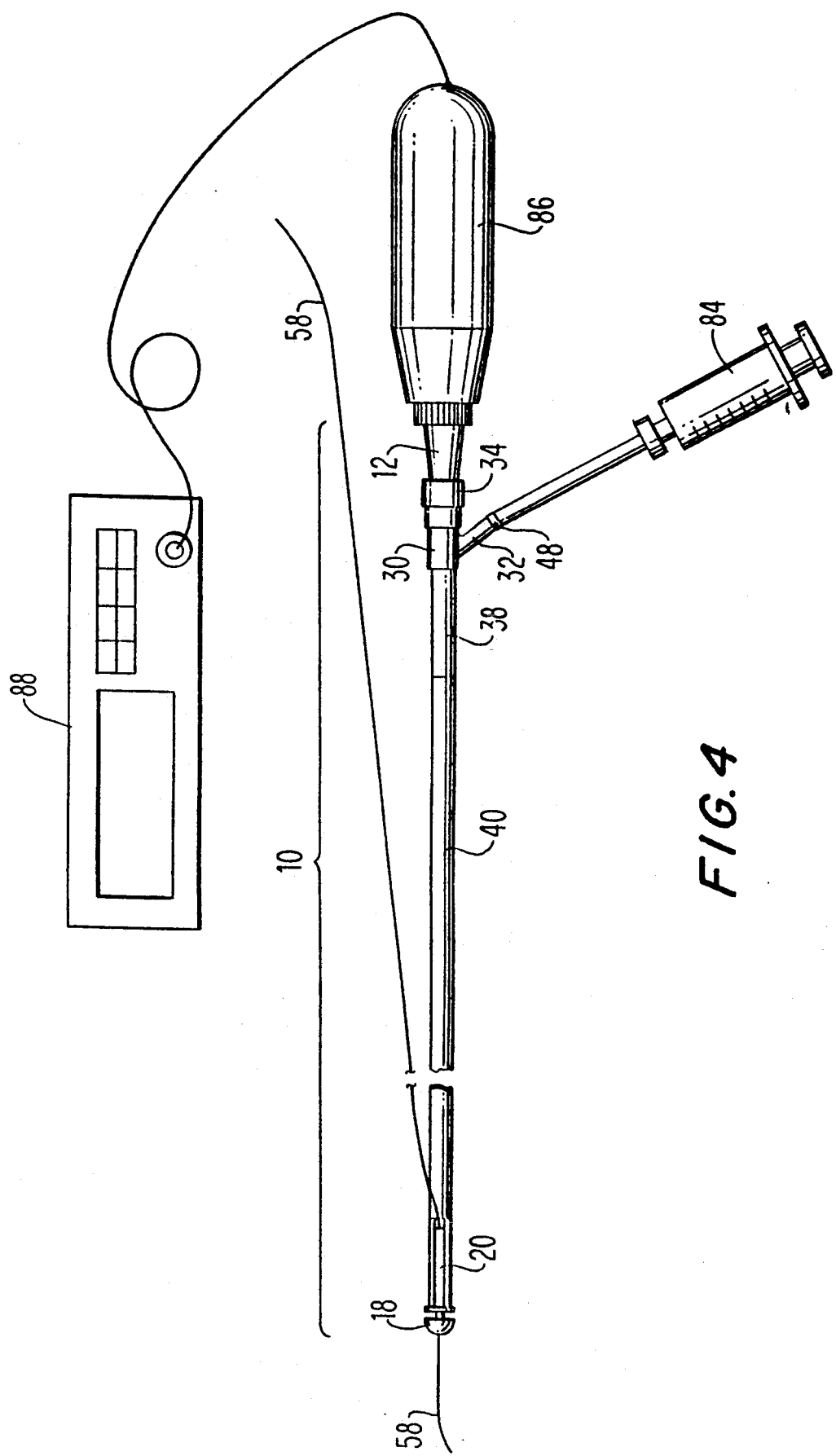
FIG. 4 is a schematic illustration of an ultrasonic system ready for use by a physician.

Before describing the manner in which the ultrasonic transmission apparatus is used and operates, reference is made to FIG. 2 which illustrates, in greater detail, the fluid conduit that surrounds transmitter 14 for supplying fluid from a suitable source to the transmitter. A portion of sleeve 40 is illustrated, and the proximal end of the sleeve is secured to the distal end of protective sheath 38. In the illustrated embodiment, the outer diameter of the proximal portion of sleeve 40 is adhesively secured to the inner diameter of the distal portion of the protective sheath. Although not clearly shown, it will be recognized that the protective sheath extends over one or more segments or transmitter 14 and preferably ends at a displacement node. The proximal end portion of protective sheath 38 is adhesively secured to input conduit 36 located at the distal end of Y-shaped coupling channel 30. As mentioned above, and as clearly shown in FIG. 2, coupling channel 30 includes a fluid supply channel 32 which, as previously referenced and as shown more particularly in FIG. 4, is connected to a syringe 84 by means of a luer lock connector 48. Thus, fluid from the syringe or, alternatively, any other desired fluid source, is supplied to sleeve 40 by way of luer lock connector 48, fluid supply channel 32, coupling channel 30, input conduit 36 and protective sheath 38.

FIG. 2 clearly illustrates O-ring 44 disposed at the location defined by annular shoulders 26 on horn 12. Coupling channel 30 includes a stepped inner diameter which forms a ledge disposed against O-ring 44. The O-ring is sandwiched between this ledge and an annular spacer 46 that is positioned about horn 12 and is disposed within coupling channel 30. The proximal end of the coupling channel is provided with screw threads that mate with cap 34, the latter having a neck which extends within the coupling channel into contact with spacer 46. It is seen that coupling channel 30, input conduit 36, O-ring 44, spacer 46 and cap 34 all are coaxial with the longitudinal axis of horn 12.

To effect a fluid-tight seal such that fluid in the channel defined by protective sheath 38 and input conduit 36 does not leak from cap 34, it will be seen that, as the cap is tightened on the proximal end of coupling channel 30, the neck of the cap drives spacer 46 against O-ring 44. Hence, a fluid-tight seal is formed between the O-ring and the ledge formed interiorly of coupling channel 30 to prevent fluid from passing beyond the O-ring and leaking from cap 34.

Figure 3C:
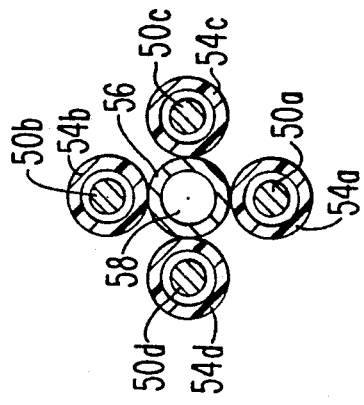
Figure 3B:
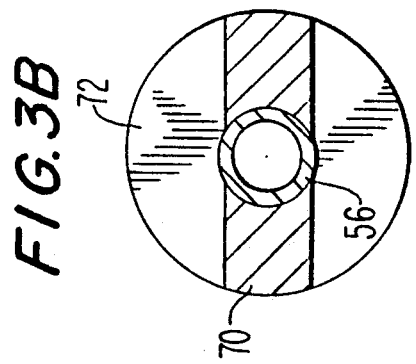
Figure 3D:
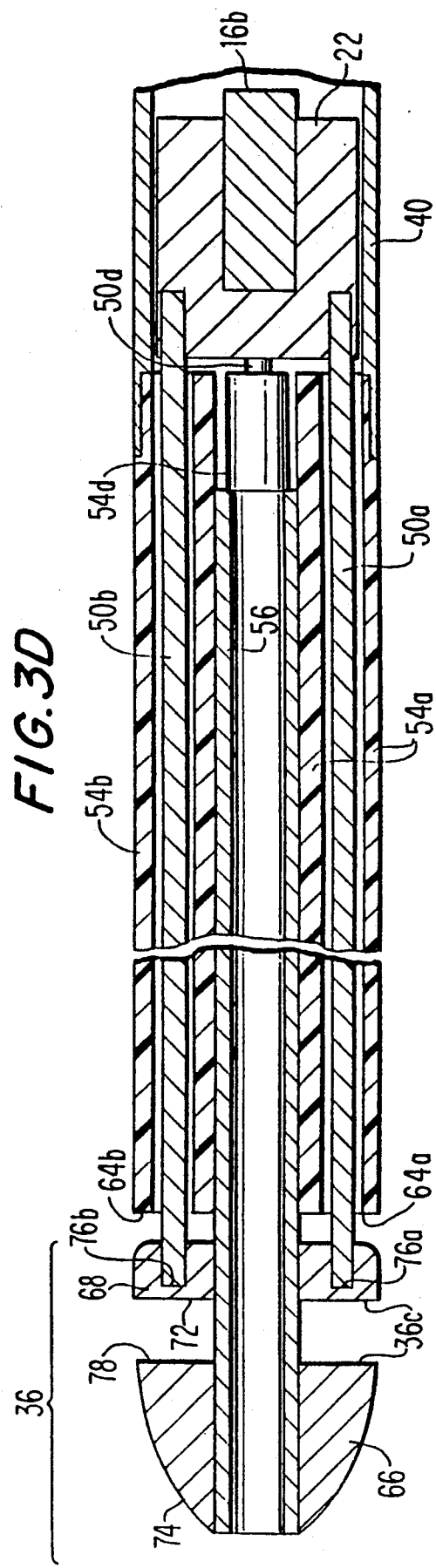

Turning now to FIGS. 3A-3D, the construction of flexible connector 20 and the manner in which the flexible connector joins tip 18 to transmitter 14 are shown in greater detail. It will be recognized that FIG. 3A is a magnified side view of flexible connector 20, FIG. 3B is a sectional view of tip 18 taken along section lines B—B of FIG. 3A, FIG. 3C is a sectional view of the flexible connector taken along section lines C—C of FIG. 3A and FIG. 3D is a sectional view of FIG. 3A. In the illustrated embodiment, the flexible connector is comprised of four wires 50a, 50b, 50c and 50d, although any other desired number of wires may be used, such as three, five, etc. The wires 50a-50d are symmetrically arranged, and each wire is surrounded by a flexible tube 54a, 54b, 54c and 54d, respectively. Although individual, discrete flexible tubes are illustrated in FIGS. 3A, 3C and 3D, a single multi-lumen conduit may be used as an alternative, as mentioned above. For convenience, however, the tubular channels which surround wires 50a-50d will be described as individual, flexible tubes.

Wires 50a-50d exhibit high tensile strength to minimize the likelihood of fracture due to fatigue or stress. As mentioned above, a desirable material from which the wires may be formed is titanium. Thus, the wires may be sufficiently thin so as to follow easily the bends of a blood vessel, but because of the high tensile strength thereof, such wires are quite strong. Nevertheless, and as described above, to minimize the risk of tip 18 breaking away from transmitter 14, a plurality of such wires is used. As also discussed above, the use of plural wires increases the level of ultrasonic energy that can be transmitted, thus reducing the input energy level that need be supplied to the transmitter for a desired tip displacement. It will be seen in FIG. 3D, and will be described further below in connection with FIG. 5, that the proximal ends of wires 50a-50d are secured to base member 22 and the distal ends of these wires are secured to tip 18.

In addition to the plural connection wires 50a-50d and their respective flexible tubes 54a-54d, a central guide wire conduit 56 is included in flexible connector 20. Those of ordinary skill in the art will recognize that, when the ultrasonic transmission apparatus is inserted into the patient's vessel lumen, a guide wire first is inserted through the vessel lumen, and the ultrasonic transmission apparatus is threaded onto this guide wire so as to be guided therealong through the lumen. To accommodate this guide wire, tip 18 is provided with a central conduit, and guide wire conduit 56 extends into this central conduit and through flexible connector 20. FIG. 3D best illustrates the positioning of this guide wire conduit, and FIG. 3C shows that guide wire conduit 56 is symmetrical with wires 50a-50d and their respective flexible tubes 54a-54d. Preferably, the proximal end of guide wire conduit 56 terminates near the proximal ends of flexible tubes 54a-54d, as seen in FIG. 3D, to facilitate the emergence of guide wire 58 from the flexible connector. As best seen in FIG. 4, it is preferred that the guide wire be external to sleeve 40 and protective sheath 38.

As shown in FIG. 3D, the length of flexible tubes 55a-54d is less than the length of the respective wires 5-0a-50d disposed therewithin. Consequently, distal openings 64a-64d of these flexible tubes are spaced from tip 18 and the fluid, such as saline, supplied thereto from coupling channel 30 (as aforedescribed in connection with FIG. 2) prevents fluid from flowing from the patient's blood vessel into the flexible tubes. FIG. 3D also illustrates the proximal ends of each of flexible tubes 54a-54d being adhesively secured in fluid-tight relation to sleeve 40. In one embodiment, the sleeve surrounds all of the flexible tubes; and FIG. 3D illustrates that the proximal ends of the flexible tubes may be provided with a shoulder for receiving and securing the distal end of the sleeve.

Tip 18 is illustrated as having a distal portion 66 of a truncated semi-spheroid shape. The tip also includes a proximal portion, which is illustrated as being substantially cylindrical, with an intermediate portion 70 connecting distal portion 66 to proximal portion 68. FIGS. 3A, 3B and 3D show that the thickness of intermediate portion 70 is less than the diameters of distal portion 66 and proximal portion 68. As a result, the surface area of tip 18 is increased, particularly in the direction normal to the direction of displacement, by reason of the discontinuity therein presented by intermediate portion 70. This discontinuity creates a cavitation surface 72 on proximal portion 68 and an opposite, facing cavitation surface 78 on distal portion 66. Other examples of tip configurations having cavitation surfaces are illustrated in FIGS. 6C and 7A-7K.

As best seen in FIG. 3D, proximal portion 68 is provided with recesses 76a, 76b, 76c and 76d adapted to receive and secure the distal ends of wires 50a, 50b, 50c and 50d. It is recognized, therefore, that the diameter of recesses 76a-76d is substantially equal to the outer diameter of wires 50a-50d, respectively. The wires may be adhesively secured within recesses 76a-76d; and it will be appreciated that other conventional means may be used to affix the wires to proximal portion 68.

FIG. 3D also illustrates the proximal ends of wires 50a-50d being secured within corresponding recesses of base member 22, with the base member including a central recess in which distal segment 16b of transmitter 14 is secured. Thus, and as described above, base member 22 functions to connect transmitter 14 to flexible connector 20.

It will be seen that, as distal segment 16b of transmitter 14 undergoes reciprocal displacement at ultrasonic frequencies, wires 50a-50d likewise are displaced reciprocally, thereby driving tip 18 at ultrasonic frequencies. Cavitation is produced by the ultrasonic displacement of the tip to destroy a thrombus in the patient's blood vessel.

Turning to FIG. 4, there is illustrated an embodiment of an ultrasonic system incorporating the ultrasonic transmission apparatus of the present invention which is seen to be connected to an ultrasonic energy source 88 and to a fluid supply syringe 84. Here, a handpiece 86 is secured to handpiece connector 24 of horn 12 (FIG. 1) and an electrical connector extends from ultrasonic energy source 88 to the handpiece. The handpiece includes an acoustic transducer and is energized by energy source 88 to supply ultrasonic energy to the horn of the transmitter, thereby driving tip 18. FIG. 4 also illustrates guide wire 58 on which tip 18 and flexible connector 20 are threaded, the guide wire serving to guide the advancement of the ultrasonic transmission apparatus through the patient's blood vessel to the vicinity of a thrombus that is to be removed. Normally, ultrasonic energy source 88 is deactivated when the illustrated ultrasonic transmission apparatus is threaded onto guide wire 58 and advanced therealong through the patient's blood vessel. Hence, during this advancement of the apparatus, the physician may grasp any portion of transmitter 14 without any adverse affect.

When tip 18 is disposed in the vicinity of the thrombus to be removed, as will be observed by conventional fluoroscopic techniques known to those of ordinary skill in the art, ultrasonic energy source 88 is activated. In the preferred embodiment, ultrasonic energy is transmitted at a frequency in the range of 40 kHz to 60 kHz, and in the application described herein, this frequency may be about 45 kHz, resulting in reciprocal displacement of tip 18 on the order of $20\mu$ to $60\mu$ peak-to-peak, and in the described application, about $30\mu$. At this time, the physician should not grasp any of segments 16a, 16b directly. It is appreciated that such direct contact of the physician's fingers with these segments will produce substantial damping of the ultrasonic displacement. But, by reason of protective sheath 38, the physician may hold transmitter 14 to provide steady and stable guiding thereof as he advances tip 18 toward the thrombus while the tip is being ultrasonically displaced. It is expected that, by grasping protective sheath 38, the physician will advance transmitter 14 until tip 18 is proximate the thrombus; and as mentioned above, the length of the sheath is sufficient to accommodate this advance. Continued ultrasonic vibration of the tip produces cavitation that destroys the thrombus, and the danger of releasing the thrombus, or a significant portion thereof, to travel through the patient's circulatory system is minimized. It should be recognized that tip design influences the flow pattern of fluid adjacent the thrombus, such as the patient's blood, saline supplied from syringe 84 (as an example of a suitable source) or a mixture thereof. In the present application, tip 18 is configured to enhance cavitation and to draw the thrombus toward the tip. However, in other applications of this invention, cavitation may be merely incidental and the tip is designed accordingly.

By reason of flexible connector 20, the distal portion of the ultrasonic transmission apparatus is readily capable of following the bends of the patient's blood vessel. The use of thin, flexible wires of high tensile strength minimizes the risk of fracture, minimizes the risk that tip 18 will break away from transmitter 14 and improves the ultrasonic energy transmission characteristics of the connector. Moreover, by forming transmitter 14 of high-Q material, the attenuation of ultrasonic displacement is minimized and, advantageously, minimal heat is generated. The use of multiple horns distributed along transmitter 14 amplifies ultrasonic displacement. Consequently, ultrasonic energy source 88 may exhibit a lower energy level to attain the same displacement of tip 18 than would otherwise be the case if significant attenuation occurred in transmitter 14.

Although not shown herein, it has been discussed above and, thus, it will be appreciated that in most applications a guiding catheter is used with guide wire 58, and the illustrated ultrasonic transmission apparatus is disposed within that guiding catheter. Of course, the physician pushes the apparatus so that tip 18 emerges from the guiding catheter and the length of protective sheath 38 should be sufficient to accommodate this movement, as described previously.

Figure 5A:
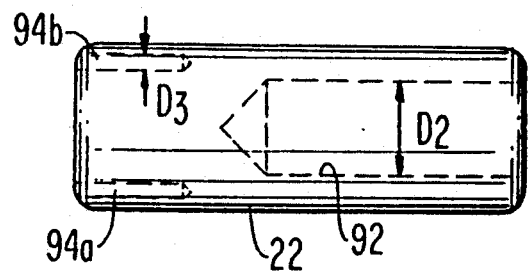
FIGS. 5A–5C are respective views of the base member that may be used with the ultrasonic transmission apparatus of the present invention.
Figure 5B:
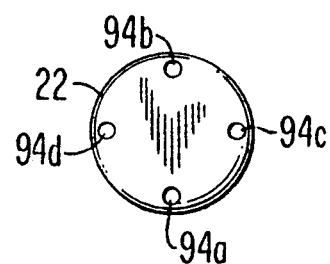
Figure 5C:
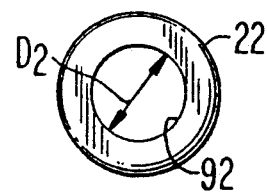

FIGS. 5A-5C illustrate a preferred embodiment of base member 22 which is used to connect the distal end of transmitter 14 to flexible connector 20. The base member provides additional stiffness and provides connections which are selected to be located at a stress node of transmitter 14. Hence, it is desirable to minimize the overall length of the base member and thereby minimize stiffness and maintain the connections at the stress node. As shown in FIG. 5A, the length of the base member is sufficient simply to provide good coupling to the distal segment 16b and good coupling to the proximal ends of wires 50a-50d. Accordingly, a central recess 92 extends from the proximal end of base member 22 (seen in FIG. 5C, which is a view taken along lines C—C) by a length which is approximately equal to the length of distal segment 16b of transmitter 14. It is seen that the diameter of recess 92 is equal to $D_2$, which is the diameter of the distal segment 16b (shown in FIG. 1A).

At the distal end of the base member, as shown in FIG. 5B, which is a distal end view taken along section lines B—B wire recesses 94a-94d are provided, each of a diameter $D_3$, which is the diameter of each of wires 50a-50d. It is appreciated that wires 50a-50d are adhesively secured in wire recesses 94a-94d; and distal segment 16b of transmitter 14 likewise is adhesively secured within recess 92. If desired, other means for affixing the wires and the distal segment to base member 22 may be used, such as those means known to those of ordinary skill in the art when interconnecting ultrasonic devices.

Base member 22, which is seen to be cylindrical, preferably is formed of the same material as transmitter 14. Thus, the base member is formed of a high mechanical Q material, preferably aluminum or aluminum alloy. Recesses 92 and 94a-94d are machined into a solid cylindrical segment, thus resulting in the illustrated base member.

A preferred embodiment of tip 18, which has been described above, is illustrated in FIGS. 6A and 6B, wherein FIG. 6B is a plan view of proximal portion 68 and FIG. 6A is a partial sectional diagram taken along lines A—A of FIG. 6B. Here, the tip is configured to enhance cavitation, although other designs that produce incidental cavitation can be used with the ultrasonic transmission apparatus of the present invention for different applications. It is seen that distal portion 66 includes a truncated semi-spheroid shape 74; and the distal portion and proximal portion 68 both are cylindrical. Intermediate portion 70, whose thickness is less than the diameter of either the distal portion or the proximal portion, is provided as a connecting member therebetween. As a result, the exterior surface of the tip undergoes a discontinuity defined by the intermediate portion, resulting in a cavitation surface 72 on proximal portion 68 and a cavitation surface 78 on distal portion 66. It is seen that each of these cavitation surfaces is substantially perpendicular to longitudinal axis 102 of tip 18.

The tip includes a center bore 104 which extends through the distal, intermediate and proximal portions thereof and is adapted to receive aforedescribed guide wire conduit 56 or to serve as a conduit for guide wire 58 (not shown). As also shown in FIGS. 6A and 6B, proximal portion 68 is provided with recesses 76a-76d to receive wires 50a-50d, respectively, of flexible connector 20. As these wires undergo ultrasonic displacement in the direction of longitudinal axis 102, tip 18 is driven at the same ultrasonic frequency to produce cavitation in the patient's blood vessel, or in any other fluid in which the ultrasonic transmission apparatus is disposed. Preferably, the tip is driven at an ultrasonic frequency in the range of about 40 kHz to 60 kHz because this frequency permits the tip to be reciprocally driven with a displacement in the range of $20\mu$ to $60\mu$ peak-to-peak without significant attenuation in flexible connector 20 due to sharp bends therein as transmitter 14 follows such bends in the patient's blood vessel. Additionally, the tip may be driven by operating energy source 88 (FIG. 4) in a pulsed mode to prevent the accumulation of, for example, fibrin particles in tip 18 when a thrombus is destroyed.

FIG. 6C illustrates a modified version of the tip shown in FIGS. 6A and 6B, in which the distal portion is substantially cylindrical and includes a concave face 80 which serves as yet an additional cavitation surface.

Figure 7A:
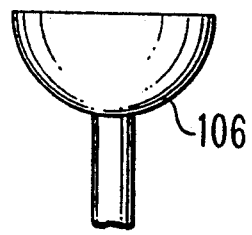
FIGS. 7A–7K illustrate various alternative embodiments of the tip that may be used with the present invention.

FIGS. 7A–7K illustrate other embodiments of tip 18 which provide sufficient cavitation when the tip is driven at ultrasonic frequencies, whereby a thrombus is destroyed. FIG. 7A illustrates a so-called reverse mushroom shape, wherein the front face of the tip is substantially planar, and the proximal portion thereof is semi-spheroid in shape.

Figure 7B:
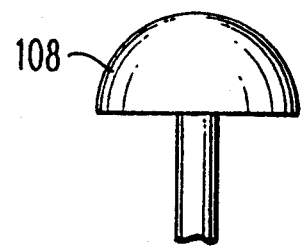

FIG. 7B illustrates a mushroom shape 108, which is seen to be the inverse, or complement, of reverse mushroom shape 106 of FIG. 7A.

Figure 7C:
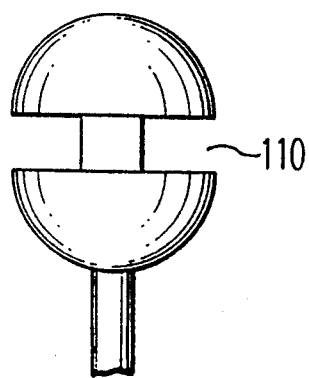

FIG. 7C illustrates a double mushroom shape 110, wherein the embodiments of FIGS. 7A and 7B are interconnected by an intermediate portion to provide two cavitation surfaces similar to aforedescribed cavitation surfaces 72 and 78 of FIG. 6A.

Figure 7D:
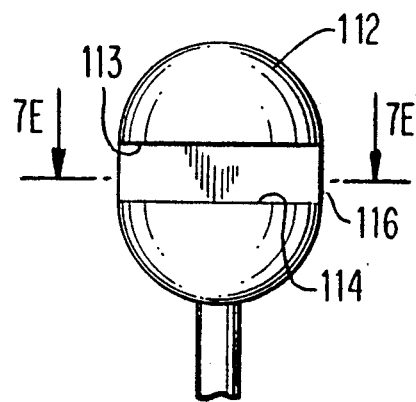

FIG. 7D illustrates another embodiment of a double mushroom shape wherein a distal semi-spheroid shape 112 is coupled to an oppositely disposed semi-spheroid shape by an intermediate section 116.

Figure 7E:
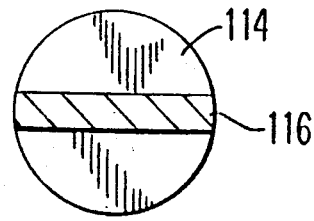

FIG. 7E, which is taken along section lines E—E of FIG. 7D shows that the thickness of intermediate section 116 is less than the diameter of, for example, distal semi-spheroid shape 112. In this configuration, two cavitation surfaces 113 and 114 are provided on the distal and proximal sections, respectively. The effect of the tip configuration shown in FIGS. 7D and 7E is substantially the same as that of the tip configuration shown in FIG. 6A.

Figure 7F:
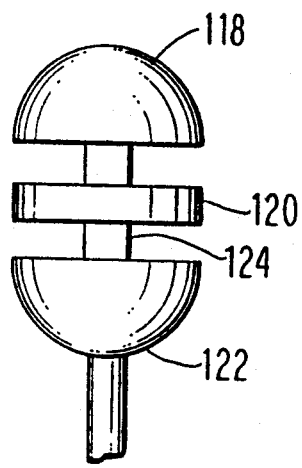

FIG. 7F illustrates a double mushroom configuration having a mushroom-shaped distal section 118 and a mushroom-shaped proximal section 122 with an intermediate section 120 disposed therebetween. The intermediate section may be disk-shaped and a center post 124 is used to connect distal section 118, intermediate section 120 and proximal section 122, as illustrated. In the configuration shown in FIG. 7F, four cavitation surfaces are provided, one on distal section 118, one on proximal section 122 and two on intermediate section 120.

Figure 7G:
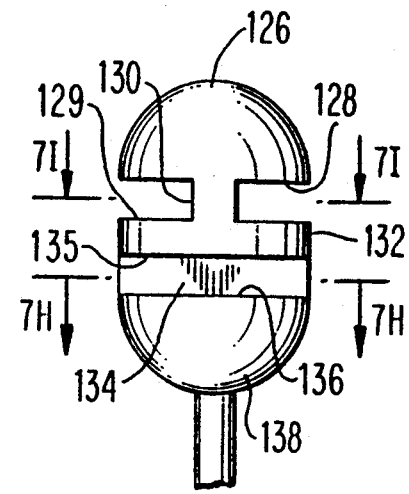
Figure 7H:
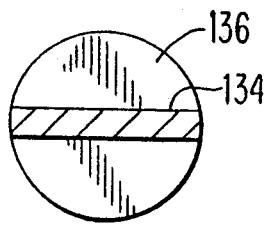
Figure 7I:
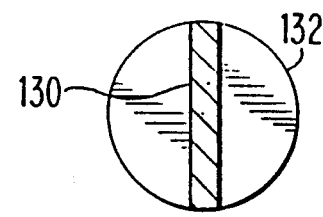

FIGS. 7G–7I illustrate yet another embodiment of tip 18, wherein a distal section 126 that is substantially mushroom-shaped is connected to a distal cavitation portion 132 by means of a connecting section 130. FIG. 7I, which is taken along section lines I—I in FIG. 7G, illustrates connecting section 130 as a relatively thin web whose thickness is less than the diameter of distal section 126, and FIG. 7I further illustrates that distal cavitation portion 132 is substantially disk-shaped. It is seen that a cavitation surface 128 is provided on distal section 126 and a cavitation surface 129 is provided on distal cavitation portion 132.

Distal cavitation portion 132 is coupled to a reverse mushroom-shaped proximal section 138 by means of an intermediate section 134, which is shown in approximate proportion in FIG. 7H, taken along section lines H—H of FIG. 7G. It is seen that intermediate section 134 is a relatively thin web similar to the thin web of connecting section 130, and rotated by about 90° with respect thereto. The thickness of intermediate section 134 is less than the diameter of proximal section 138. Accordingly, cavitation surface 136 is provided on proximal section 138 and a cavitation surface 135 is provided on distal cavitation portion 132 in facing relation thereto. In the embodiment shown in FIGS. 7G–7I, for cavitation surfaces are provided, one on distal section 126, two on distal cavitation portion 132 and one on proximal section 138. The cavitation effect produced by the tip shown in FIGS. 7G–7I is substantially similar to the cavitation effect produced by the tip shown in FIG. 7F.

Figure 7J:
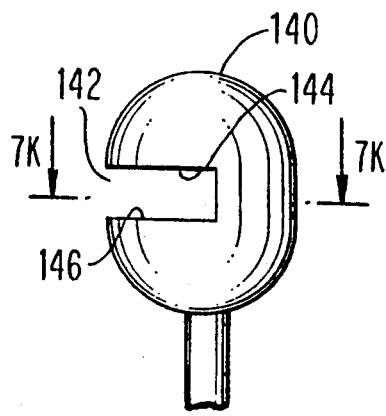
Figure 7K:
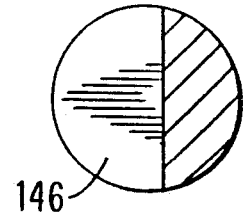

FIG. 7J illustrates yet another embodiment of a tip having an increased surface for producing cavitation. Here, the tip is shown as an elongated semi-spheroid shape 140 having a notch 142 in the central portion thereof, resulting in a discontinuity in the exterior surface to define cavitation surfaces 144 and 146. FIG. 7K is taken along section lines K—K of FIG. 7J and illustrates the shape of cavitation surface 146. It will be appreciated that cavitation surface 144 is substantially similar in shape.

Tests have been conducted on the preferred embodiment of the present invention which confirm the improved results attained thereby. These tests, based upon the embodiment illustrated in FIGS. 1, 2, 4 and 6, are summarized as follows:

DISPLACEMENT

Transmitter 14, connector 20 and tip 18 were inserted into an anatomic model leading to the left anterior descending (LAD) coronary artery. Puncture site was at the femoral artery and tip 18 reached the LAD by way of a 9-French Judkins left coronary guide catheter. Tip displacement was observed and measured by conventional video magnification, with the following results:

| Input Power | Displacement (microns) |
| --- | --- |
| 8 watts | 17.2 peak-to-peak |
| 10 | 20.0 |
| 12 | 25.7 |
| 14 | 31.5 |
| 16 | 34.3 |
| 18 | 38.6 |

DISPLACEMENT COMPARISON

A comparison of the displacement attained by the ultrasonic transmission apparatus of the present invention with apparatus of the type described in application Ser. No. 449,465 was conducted. The embodiment of the present invention was 126 cm in overall length, and transmitter 14 was formed with four horn segments distributed along its length and interspersed with straight segments. The diameter $D_1$ of the transmitter at its proximal end was 1.6 mm and the diameter $D_2$ of the transmitter at its distal end was 0.5 mm. The apparatus to which the present invention was compared was formed of a wire 125.5 cm long of constant, uniform diameter of 0.5 mm along its entire length (referred to herein as the "straight wire transmitter"). Both transmitters were coupled to horns (such as horn 12) of substantially the same profile and both transmitters were energized at about 28.5 kHz. A model A-200A Branson Horn Analyzer was used for testing.

No Bend: When both transmitters were tested at the same input power levels in a straight water tank having no bend imparted to the transmitter, the tip displacement of the present invention was measured at 65.8μ and the tip displacement of the straight wire transmitter was measured at 11.4μ, only 17% of the displacement attained by the present invention.

Bend: The two transmitters were disposed (one at a time) in a plastic tube bent by 180° to form a curve whose diameter was 9 cm; and the plastic tubes were located in the aforementioned water tank. Tip displacement of the present invention subjected to this bend was measured at 42.9μ and tip displacement of the straight wire transmitter was measured at less than 2.8μ. Thus, by reason of the bend in the transmitters, tip displacement is reduced, but this reduction is only about 34% of no-bend displacement for the present invention as compared to about 75% for the straight wire transmitter.

Flexibility: The flexibility of the tip connected to transmitter 14 by connector 20 of the present invention was compared to the flexibility of the tip of the straight wire transmitter by measuring the force needed to deflect the tip by 1 mm. For this comparison the transmitter was clamped near its distal end such that the distance from the clamp to the center of gravity of the tip was 1.3 cm. In the present invention, the connector was formed of four titanium wires, each of 0.25 mm diameter and the straight wire transmitter had a diameter of 0.5 mm. In both transmitters, the cross-sectional areas (that is, the cross-sectional area of the four titanium wires and the cross-sectional area of the straight wire transmitter) were 0.196 mm². The bending force needed to achieve a 1 mm tip deflection of the present invention was 7 grams and the bending force needed to achieve a 1 mm tip deflection of the straight wire transmitter was 35 grams.

THROMBOLYSIS

Thrombolysis efficacy of the ultrasonic transmission apparatus was tested empirically on samples of bovine thrombus placed in the LAD. Thrombolysis commenced with input power set at 12 watts and became more consistent once this input power reached 14 watts. The time needed for the apparatus to clear a lesion varied with different thrombus samples from about 5 seconds to more than 60 seconds. The effect of drawing the thrombus to tip 18 was clearly observed, even with flow in the LAD of about 10 to 20 ml/min.

SUMMARY

While the present invention has been particularly shown and described with reference to preferred embodiments, it will be readily appreciated that various changes may be made without departing from the spirit and scope of the invention. For example, the tips shown in FIGS. 7A-7K may be provided with a concave face at the distal end thereof. In addition, although several examples of tip configurations have been shown and described herein, it will be recognized that other configurations may be used, if desired. It is preferred, however, that the tip exhibit an increase in surface area so as to provide optimum cavitation for destroying thrombi. Nevertheless, in different applications of the present invention, the tip will be configured so as not to generate substantial cavitation.

It is intended that the appended claims be interpreted as covering the embodiments disclosed herein, those variations and changes which have been discussed above, and all equivalents thereto.

What is claimed is:

1. Ultrasonic transmission apparatus comprising:
   a horn connectable to an energy source for amplifying ultrasound displacement;
   transmission means formed of material having relatively high mechanical Q for transmitting ultrasonic energy therethrough at a frequency f and comprised of multiple ultrasonic horn-shaped segments distributed longitudinally along said transmission means, each horn-shaped segment having a length substantially equal to a multiple of $\lambda/2$, where $\lambda = c/f$ (c is the speed of sound in said material), the transmission means having a proximal end of cross-sectional diameter $D_1$ connected to said horn and a distal end of cross-sectional diameter $D_2$, where $D_1 > D_2$;
   a tip driven by said ultrasonic energy; and
   flexible means having a first end connected to the distal end of said transmission means and a second end connected to said tip for transferring to said tip the ultrasonic energy which is received from said transmission means.

2. The apparatus of claim 1 wherein said flexible means is comprised of plural wires, each of a diameter less than $D_2$.

3. The apparatus of claim 2 wherein said flexible means further includes means for isolating each of said plural wires.

4. The apparatus of claim 3 further including a base member coupling ends of said plural wires to said distal end of said transmission means.

5. The apparatus of claim 4 wherein said base member has a length $L_b$, said flexible means has a length L and said tip has a length $L_t$ and $L + L_b + L_t = k \lambda'/2$, where k is an integer, $\lambda' = c'/f$, c' is the effective speed of sound through said base member, said flexible means and said tip, and f is the frequency of said ultrasonic energy.

6. The apparatus of claim 4 wherein said base member comprises a generally cylindrical housing having a central recess of diameter substantially equal to $D_2$ open at one end of said housing receiving said distal end of said transmission means, and plural recesses open at an opposite end of said housing receiving the first ends of said plural wires.

7. The apparatus of claim 3 wherein said means for isolating each of said plural wires comprises tubular channel means for disposal about said wires.

8. The apparatus of claim 7 wherein said tubular channel means is comprised of plural flexible tubes, each disposed about a respective wire.

9. The apparatus of claim 7 wherein said transmission means is further comprised of straight segments interspersed with said horn-shaped segments, each straight segment having a length substantially equal to a multiple of $\lambda/2$.

10. The apparatus of claim 9 wherein said transmission means further comprises a sleeve disposed about at least those of said horn-shaped and straight segments expected to be inserted in a lumen with which said apparatus is used, said sleeve having a proximal end portion and a distal end portion secured to said tubular channel means.

11. The apparatus of claim 10 wherein said sleeve is of flexible material and has an inner diameter which, at any longitudinal location thereof, is greater than the diameter of said transmission means at the same longitudinal location.

12. The apparatus of claim 10 wherein said tubular channel means has a distal end spaced from said tip and open to permit fluid to flow through said tubular channel means.

13. The apparatus of claim 12 wherein said sleeve has an inner diameter spaced from said transmission means to define a fluid channel; and further comprising fluid supply means for supplying fluid through said fluid channel to said tubular channel means to provide a lubricant for and to reduce the transverse vibration of said transmission means.

14. The apparatus of claim 13 wherein said fluid supply means comprises an input conduit coupled to said sleeve in the vicinity of said proximal end portion thereof for coupling fluid thereto, and valve means in fluid communication with said proximal end portion of said sleeve to prevent backflow of fluid through said sleeve.

15. The apparatus of claim 14 wherein said fluid supply means further includes a coupling channel for coupling said proximal end portion of said sleeve to said horn, and wherein said valve means comprises a manually tightened cap disposed over said coupling channel and said horn and operable to seal an O-ring at a node of longitudinal, ultrasonic vibration.

16. The apparatus of claim 15 wherein said horn is provided with a pair of annular shoulders at said node of longitudinal ultrasonic vibration to define the location of said O-ring.

17. The apparatus of claim 13 further including a protective sheath coupled in fluid tight relation to said sleeve and disposed over at least one segment at the proximal end of said transmission means to enable a user to grasp said proximal end when guiding said transmission means into the lumen without substantially damping ultrasonic vibrations of said transmission means.

18. The apparatus of claim 17 wherein said at least one segment over which said protective sheath is disposed is provided with plural annular shoulders located at nodes of ultrasonic vibration to contact said sheath in the event said sheath is deformed; said sheath having an inner diameter spaced from said transmission means to define a fluid conduit in fluid communication with the fluid channel of said sleeve.

19. The apparatus of claim 18 wherein said means for supplying fluid to said channel is coupled to said protective sheath; and wherein said fluid additionally prevents backflow through said tubular channel means and said fluid channel to said fluid conduit.

20. The apparatus of claim 2 wherein each of the wires of said flexible means is formed of material having a tensile strength different than that of the material of said transmission means.

21. The apparatus of claim 2 wherein said transmission means is formed of aluminum and the wires of said flexible means are formed of titanium.

22. The apparatus of claim 21 wherein said horn and transmission means are of unitary construction.

23. The apparatus of claim 1 wherein said transmission means includes straight segments each of a length that is a multiple of $\lambda/2$ and interspersed with said horn-shaped segments, the transmission means further including a protective sheath disposed over at least one segment at the proximal end of said transmission means and formed of relatively rigid material which, when grasped by a user, does not deform into contact with said transmission means and thereby damp ultrasonic vibrations thereof.

24. The apparatus of claim 23 wherein the protective sheath has a distal end located substantially at a node of ultrasonic vibration in said transmission means.

25. The apparatus of claim 1 wherein said tip is configured to enhance cavitation in a fluid.

26. The apparatus of claim 25 wherein said tip is comprised of proximal and distal portions having respective diameters and interconnected by an intermediate portion having a thickness less than the diameter of each of said proximal and distal portions, said proximal, intermediate and distal portions having a common longitudinal axis.

27. The apparatus of claim 26 wherein said proximal, distal and intermediate portions are of unitary construction and said flexible means is secured to said proximal portion.

28. The apparatus of claim 26 wherein said distal portion is of substantially truncated semi-spheroid shape and said proximal portion is of cylindrical shape.

29. The apparatus of claim 26 wherein said distal and proximal portions both are of cylindrical shape.

30. The apparatus of claim 29 wherein said distal portion has a concave-shaped face.

31. The apparatus of claim 26 wherein said proximal, intermediate and distal portions have a common longitudinal channel to receive a guide wire for guiding said tip, and thereby said flexible means and said transmission means, through a lumen.

32. The apparatus of claim 31 wherein said flexible means includes a center channel in communication with said common longitudinal channel for receiving said guide wire.

33. The apparatus of claim 32 further comprising a central guide wire conduit disposed in said common longitudinal channel and said center channel for guiding said guide wire through said tip and through said flexible means.

34. The apparatus of claim 26 wherein the diameter of the proximal portion is substantially equal to the diameter of the distal portion.

35. The apparatus of claim 1 wherein said transmission means includes straight segments separating said horn-shaped segments, each straight segment having a length substantially equal to a multiple of $\lambda/2$.

36. The apparatus of claim 35 wherein the length of a straight segment disposed between successive horn-shaped segments differs from the length of either of said successive horn-shaped segments.

37. The apparatus of claim 35 wherein each horn-shaped segment has a distal end diameter less than its proximal end diameter.

38. Ultrasonic transmission apparatus comprising:
an input horn connectable to an energy source for amplifying ultrasound displacement;
a horn-shaped transmitter formed of material having relatively high mechanical Q for transmitting ultrasonic energy therethrough at a frequency f and having a length substantially equal to a multiple of $\lambda/2$, where $\lambda=c/f$ (c is the speed of sound in said material), the horn-shaped transmitter having a proximal end of cross-sectional diameter $D_1$, connected to said input horn and a distal end of cross-sectional diameter $D_2$, wherein $D_1>D_2$;
a tip driven by said ultrasonic energy; and
flexible means having a first end connected to the distal end of said horn-shaped transmitter and a second end connected to said tip for transferring to said tip the ultrasonic energy which is received from said horn-shaped transmitter, said flexible means being comprised of plural wires, each of a diameter less than $D_2$.

39. The apparatus of claim 38 wherein said flexible means includes means for isolating each of said plural wires.

40. The apparatus of claim 39 wherein each of said wires is formed of material having a tensile strength different than that of the material of said horn-shaped transmitter.

41. The apparatus of claim 40 wherein said means for isolating each of said plural wires comprises tubular channel means for disposal about said wires.

42. The apparatus of claim 41 wherein said tubular channel means is comprised of plural flexible tubes, each disposed about a respective wire.

43. The apparatus of claim 41 wherein at least a portion of said horn-shaped transmitter is disposed in a sleeve, the sleeve being formed of flexible material and having a distal end portion secured to said tubular channel means and a proximal end portion.

44. The apparatus of claim 43 wherein said tubular channel means has a distal end spaced from said tip and open to permit fluid to flow through said tubular channel means.

45. The apparatus of claim 43 further comprising fluid supply means for supplying fluid through said sleeve to said tubular channel means to provide a lubricant for and to reduce transverse vibration of said horn-shaped transmitter.

46. The apparatus of claim 45 further including a protective sheath coupled in fluid tight relation to said sleeve and disposed over a proximal portion of said horn-shaped transmitter to enable a user to grasp said proximal portion when guiding the transmitter into a lumen without substantially damping ultrasonic vibrations of said transmitter.

47. The apparatus of claim 46 wherein said protective sheath, said sleeve and said tubular channel means comprise a fluid conduit from said fluid supply means to said tip; and wherein said fluid additionally prevents backflow through said fluid conduit.

48. The apparatus of claim 38 wherein the horn-shaped transmitter is formed of aluminum and the wires of said flexible means are formed of titanium.

49. A tip for use in ultrasonic transmission apparatus driven for longitudinal, reciprocating displacement, comprising a proximal portion connectable to an ultrasonic transmitter, a distal portion and an intermediate portion connecting said proximal and distal portions, the proximal and distal portions having respective diameters and the intermediate portion having a thickness less than the diameter of each of said proximal and distal portions, said proximal, distal and intermediate portions having a common longitudinal axis, said distal portion being of substantially truncated semi-spheroid shape and having a first front face and said proximal portion being of cylindrical shape.

50. A tip for use in ultrasonic transmission apparatus driven for longitudinal, reciprocating displacement, comprising a proximal portion connectable to an ultrasonic transmitter, a distal portion and an intermediate portion connecting said proximal and distal portions, the proximal and distal portions having respective diameters and the intermediate portion having a thickness less than the diameter of each of said proximal and distal portions, said proximal, distal and intermediate portions having a common longitudinal axis, said distal portion being mushroom-shaped and said proximal portion being reverse mushroom-shaped.

51. A tip for use in ultrasonic transmission apparatus driven for longitudinal, reciprocating displacement, comprising a proximal portion connectable to an ultrasonic transmitter, a distal portion and an intermediate portion connecting said proximal and distal portions, the proximal and distal portions having respective diameters and the intermediate portion having a thickness less than the diameter of each of said proximal and distal portions, said proximal, distal and intermediate portions having a common longitudinal axis, and a disk-shaped intermediate section secured to said intermediate portion and disposed between said distal and proximal portions.

* * * * *

UNITED STATES PATENT AND TRADEMARK OFFICE
CERTIFICATE OF CORRECTION

PATENT NO. : 5,269,297
DATED : December 14, 1993
INVENTOR(S) : Li Weng, et al

It is certified that error appears in the above-indentified patent and that said Letters Patent is hereby corrected as shown below:

Column 20:
    Claim 4, line 2, column 20, line 29, after "coupling" insert --first--.

Claim 5, line 3, column 20, line 33, change "$\lambda/2$" to --$\lambda'/2$--.

Claim 11, line 1, column 20, line 62, after "is" insert --formed--.

Column 24:
    Claim 49, line 12, column 24, line 15, delete "and" (first occurrence); before "front" change "first" to --flat--.

Signed and Sealed this

Eighteenth Day of October, 1994

Attest:

BRUCE LEHMAN

*Attesting Officer*      *Commissioner of Patents and Trademarks*